(12) United States Patent
Bumbalough

(10) Patent No.: US 8,034,108 B2
(45) Date of Patent: Oct. 11, 2011

(54) INTRAOCULAR LENS HAVING A HAPTIC THAT INCLUDES A CAP

(75) Inventor: Timothy R. Bumbalough, Fullerton, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 381 days.

(21) Appl. No.: 12/057,633

(22) Filed: Mar. 28, 2008

(65) Prior Publication Data
US 2009/0248152 A1 Oct. 1, 2009

(51) Int. Cl.
*A61F 2/16* (2006.01)
(52) U.S. Cl. ....... 623/6.43; 623/6.4; 623/6.41; 623/6.46
(58) Field of Classification Search ............... 623/4.1, 623/6.11, 6.38, 6.4, 6.62, 6.13, 6.34, 6.37, 623/6.41, 6.43, 6.46
See application file for complete search history.

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1943 | Houchin |
| 2,405,989 A | 6/1946 | Beach |
| 2,511,517 A | 6/1950 | Spiegel |
| 2,834,023 A | 5/1958 | Lieb |
| 3,004,470 A | 10/1961 | Ruhle |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |

(Continued)

FOREIGN PATENT DOCUMENTS
AU    3225789    10/1989
(Continued)

OTHER PUBLICATIONS

U.S. Appl. No. 10/280,918, filed Aug. 5, 2003.
(Continued)

*Primary Examiner* — David Isabella
*Assistant Examiner* — Seema Swaminathan

(57) ABSTRACT

An intraocular lens is disclosed, with an adjustable optic that changes shape in response to a deforming force exerted by the zonules of the eye. A haptic supports the optic around its equator and couples the optic to the capsular bag of the eye. The haptic may include a cap on the anterior and/or posterior surfaces of the lens. The lens may include a force transfer member, such as a hinge, that couples forces from the haptic to the cap, so that a radial force on the haptic changes the curvature of the cap. The haptic and optic may be refractive index-matched. The cap may be made of the haptic material, which is stiffer than the optic material, and can influence the deformation of the lens during accommodation. A cap on the anterior surface may produce an axial movement of the lens in an anterior direction during accommodation. The cap may also protect the surfaces of the optic during handling and installation. The posterior surface of the lens may be shaped so that it does not significantly offset the contributions of the anterior surface during accommodation.

41 Claims, 19 Drawing Sheets

SECTION B-B

U.S. PATENT DOCUMENTS

| | | |
|---|---|---|
| 3,673,616 A | 7/1972 | Fedorov et al. |
| 3,693,301 A | 9/1972 | Lemaltre |
| 3,711,870 A | 1/1973 | Deltrick |
| 3,718,870 A | 2/1973 | Keller |
| 3,794,414 A | 2/1974 | Wesley |
| 3,866,249 A | 2/1975 | Fiom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,055,378 A | 10/1977 | Feneberg et al. |
| 4,503,953 A | 10/1977 | Fiom et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,244,060 A | 1/1981 | Hoffer |
| 4,244,597 A | 1/1981 | Dandle |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl et al. |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsuetaki et al. |
| 4,693,716 A | 9/1987 | Mackool |
| RE32,525 E | 10/1987 | Pannu |
| 4,702,244 A | 10/1987 | Mazzocco |
| 4,704,016 A | 11/1987 | de Carle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |

| Patent | Kind | Date | Inventor | Ref |
|---|---|---|---|---|
| 5,423,929 | A * | 6/1995 | Doyle et al. | 156/73.1 |
| RE34,988 | E | 7/1995 | Yang et al. | |
| 5,443,506 | A | 8/1995 | Garabet | |
| 5,476,514 | A | 12/1995 | Cumming | |
| 5,480,428 | A | 1/1996 | Fedorov et al. | |
| 5,489,302 | A | 2/1996 | Skottun | |
| 5,496,366 | A | 3/1996 | Cumming | |
| 5,521,656 | A | 5/1996 | Portney | |
| 5,562,731 | A | 10/1996 | Cumming | |
| 5,574,518 | A | 11/1996 | Mercure | |
| 5,578,081 | A | 11/1996 | McDonald | |
| 5,593,436 | A | 1/1997 | Langerman | |
| 5,607,472 | A | 3/1997 | Thompson | |
| 5,628,795 | A | 5/1997 | Langerman | |
| 5,628,796 | A | 5/1997 | Suzuki | |
| 5,628,797 | A | 5/1997 | Richer | |
| 5,652,014 | A | 7/1997 | Galin et al. | |
| 5,652,638 | A | 7/1997 | Roffman et al. | |
| 5,657,108 | A | 8/1997 | Portney | |
| 5,674,282 | A | 10/1997 | Cumming | |
| 5,682,223 | A | 10/1997 | Menezes et al. | |
| 5,684,560 | A | 11/1997 | Roffman et al. | |
| 5,766,244 | A | 6/1998 | Binder | |
| 5,769,890 | A | 6/1998 | McDonald | |
| 5,776,191 | A | 7/1998 | Mazzocco | |
| 5,776,192 | A | 7/1998 | McDonald | |
| 5,814,103 | A | 9/1998 | Lipshitz et al. | |
| 5,824,074 | A | 10/1998 | Koch | |
| 5,843,188 | A | 12/1998 | McDonald | |
| 5,847,802 | A | 12/1998 | Menezes et al. | |
| 5,876,442 | A | 3/1999 | Lipshitz et al. | |
| 5,898,473 | A | 4/1999 | Seidner et al. | |
| 5,968,094 | A | 10/1999 | Werblin et al. | |
| 5,984,962 | A | 11/1999 | Anello et al. | |
| 6,013,101 | A | 1/2000 | Israel | |
| 6,051,024 | A | 4/2000 | Cumming | |
| 6,083,261 | A | 7/2000 | Callahan et al. | |
| 6,096,078 | A | 8/2000 | McDonald | |
| 6,110,202 | A | 8/2000 | Barraquer et al. | |
| 6,117,171 | A | 9/2000 | Skottun | |
| 6,120,538 | A | 9/2000 | Rizzo, III et al. | |
| 6,136,026 | A | 10/2000 | Israel | |
| 6,152,958 | A | 11/2000 | Nordan | |
| 6,176,878 | B1 | 1/2001 | Gwon et al. | |
| 6,197,058 | B1 | 3/2001 | Portney | |
| 6,197,059 | B1 | 3/2001 | Cumming | |
| 6,200,342 | B1 * | 3/2001 | Tassignon | 623/6.37 |
| 6,217,612 | B1 | 4/2001 | Woods | |
| 6,231,603 | B1 | 5/2001 | Lang et al. | |
| 6,299,641 | B1 | 10/2001 | Woods | |
| 6,302,911 | B1 | 10/2001 | Hanna | |
| 6,322,589 | B1 | 11/2001 | Cumming | |
| 6,399,734 | B1 | 6/2002 | Hodd et al. | |
| 6,406,494 | B1 | 6/2002 | Laguette et al. | |
| 6,443,985 | B1 | 9/2002 | Woods | |
| 6,485,516 | B2 | 11/2002 | Boehm | |
| 6,488,708 | B2 | 12/2002 | Sarfarazi | |
| 6,503,276 | B2 | 1/2003 | Lang et al. | |
| 6,524,340 | B2 | 2/2003 | Israel | |
| 6,551,354 | B1 | 4/2003 | Ghazizadeh et al. | |
| 6,554,859 | B1 | 4/2003 | Lang et al. | |
| 6,558,420 | B2 | 5/2003 | Green | |
| 6,559,317 | B2 | 5/2003 | Hupperts, III et al. | |
| 6,592,621 | B1 | 7/2003 | Domino | |
| 6,599,317 | B1 | 7/2003 | Weinschenk, III et al. | |
| 6,616,691 | B1 | 9/2003 | Tran | |
| 6,616,692 | B1 | 9/2003 | Glick et al. | |
| 6,638,305 | B2 | 10/2003 | Laguette | |
| 6,638,306 | B2 | 10/2003 | Cumming | |
| 6,645,246 | B1 | 11/2003 | Weinschenk, III et al. | |
| 6,660,035 | B1 | 12/2003 | Lang et al. | |
| 6,749,633 | B1 | 6/2004 | Lorenzo et al. | |
| 6,749,634 | B2 | 6/2004 | Hanna | |
| 6,855,164 | B2 | 2/2005 | Glazier | |
| 6,930,838 | B2 | 8/2005 | Schachar | |
| 7,018,409 | B2 | 3/2006 | Glick et al. | |
| 7,025,783 | B2 | 4/2006 | Brady et al. | |
| 7,097,660 | B2 | 8/2006 | Portney | |
| 7,125,422 | B2 | 10/2006 | Woods et al. | |
| 7,150,759 | B2 | 12/2006 | Paul et al. | |
| 7,179,292 | B2 * | 2/2007 | Worst et al. | 623/6.43 |
| 7,220,279 | B2 | 5/2007 | Nun | |
| 7,223,288 | B2 | 5/2007 | Zhang et al. | |
| 7,503,938 | B2 | 3/2009 | Phillips | |
| 7,815,678 | B2 | 10/2010 | Ben Nun | |
| 2002/0111678 | A1 | 8/2002 | Zadno-Azizi et al. | |
| 2002/0116058 | A1 | 8/2002 | Zadno-Azizi et al. | |
| 2002/0120329 | A1 | 8/2002 | Lang et al. | |
| 2002/0161434 | A1 * | 10/2002 | Laguette et al. | 623/6.16 |
| 2002/0188351 | A1 | 12/2002 | Laguette | |
| 2003/0004569 | A1 | 1/2003 | Haefliger | |
| 2003/0060878 | A1 | 3/2003 | Shadduck | |
| 2003/0060881 | A1 | 3/2003 | Glick et al. | |
| 2003/0109926 | A1 | 6/2003 | Portney | |
| 2003/0130732 | A1 | 7/2003 | Sarfarazi | |
| 2003/0135272 | A1 | 7/2003 | Brady et al. | |
| 2003/0149480 | A1 | 8/2003 | Shadduck | |
| 2003/0187505 | A1 | 10/2003 | Liao | |
| 2003/0204254 | A1 | 10/2003 | Peng et al. | |
| 2003/0204255 | A1 | 10/2003 | Peng et al. | |
| 2004/0054408 | A1 | 3/2004 | Glick et al. | |
| 2004/0082993 | A1 | 4/2004 | Woods | |
| 2004/0082994 | A1 | 4/2004 | Woods et al. | |
| 2004/0082995 | A1 | 4/2004 | Woods | |
| 2004/0111153 | A1 | 6/2004 | Woods et al. | |
| 2004/0158322 | A1 | 8/2004 | Shen | |
| 2004/0167621 | A1 | 8/2004 | Peyman | |
| 2004/0181279 | A1 | 9/2004 | Nun | |
| 2004/0215340 | A1 | 10/2004 | Messner et al. | |
| 2005/0018504 | A1 | 1/2005 | Marinelli et al. | |
| 2005/0021139 | A1 | 1/2005 | Shadduck | |
| 2005/0027354 | A1 | 2/2005 | Brady et al. | |
| 2005/0085906 | A1 | 4/2005 | Hanna | |
| 2005/0085907 | A1 | 4/2005 | Hanna | |
| 2005/0125057 | A1 | 6/2005 | Cumming | |
| 2005/0131535 | A1 | 6/2005 | Woods | |
| 2005/0137703 | A1 | 6/2005 | Chen | |
| 2005/0288785 | A1 | 12/2005 | Portney et al. | |
| 2006/0064162 | A1 | 3/2006 | Klima | |
| 2006/0111776 | A1 | 5/2006 | Glick et al. | |
| 2006/0116765 | A1 | 6/2006 | Blake et al. | |
| 2006/0238702 | A1 | 10/2006 | Glick et al. | |
| 2007/0078515 | A1 | 4/2007 | Brady | |
| 2007/0100444 | A1 * | 5/2007 | Brady et al. | 623/6.37 |
| 2007/0106381 | A1 | 5/2007 | Blake | |
| 2007/0129798 | A1 | 6/2007 | Chawdhary | |
| 2007/0135915 | A1 | 6/2007 | Klima | |
| 2007/0213817 | A1 | 9/2007 | Esch et al. | |
| 2007/0260309 | A1 | 11/2007 | Richardson | |
| 2007/0299487 | A1 | 12/2007 | Shadduck | |
| 2008/0161913 | A1 | 7/2008 | Brady | |
| 2008/0161914 | A1 | 7/2008 | Brady | |
| 2009/0012609 | A1 | 1/2009 | Geraghty | |

FOREIGN PATENT DOCUMENTS

| | | |
|---|---|---|
| CH | 681687 | 5/1993 |
| DE | 2702117 | 7/1978 |
| DE | 3246306 | 6/1984 |
| DE | 4038088 | 6/1992 |
| DE | 19501444 | 7/1996 |
| EP | 0064812 | 11/1982 |
| EP | 0246216 | 11/1987 |
| EP | 0328117 | 8/1989 |
| EP | 0329981 | 8/1989 |
| EP | 0337390 | 10/1989 |
| EP | 0342895 | 11/1989 |
| EP | 0351471 | 1/1990 |
| EP | 0356050 | 2/1990 |
| EP | 0488835 | 6/1992 |
| EP | 0507292 | 10/1992 |
| EP | 0566170 | 10/1993 |
| EP | 0601845 | 6/1994 |
| EP | 0691109 | 1/1996 |
| EP | 0897702 | 2/1999 |
| EP | 0766540 | 4/1999 |
| EP | 766540 B1 | 8/1999 |
| GB | 2058391 | 4/1981 |
| GB | 2124500 | 2/1984 |

| | | |
|---|---|---|
| GB | 2129155 | 5/1984 |
| GB | 2146791 | 4/1985 |
| GB | 2192291 | 1/1988 |
| GB | 2215076 | 9/1989 |
| JP | 2126847 | 5/1990 |
| WO | 86/03961 | 7/1986 |
| WO | 87/00299 | 1/1987 |
| WO | 87/07496 | 12/1987 |
| WO | 89/02251 | 3/1989 |
| WO | 89/11672 | 11/1989 |
| WO | 90/00889 | 2/1990 |
| WO | 93/05733 | 4/1993 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/27825 | 8/1997 |
| WO | 97/43984 | 11/1997 |
| WO | 98/56315 | 12/1998 |
| WO | 00/61036 | 4/2000 |
| WO | 00/27315 | 5/2000 |
| WO | 00/66039 | 11/2000 |
| WO | 01/19288 | 3/2001 |
| WO | 01/34066 | 5/2001 |
| WO | 01/34067 | 5/2001 |
| WO | 02/19949 | 3/2002 |
| WO | 03/015669 | 2/2003 |
| WO | 03/034949 | 5/2003 |
| WO | 03/059208 | 7/2003 |
| WO | 03/075810 | 9/2003 |
| WO | 2005/018504 | 3/2005 |
| WO | WO2005115278 A1 | 12/2005 |
| WO | 2007/040964 | 4/2007 |
| WO | 2007/067872 | 6/2007 |
| WO | WO2007067872 | 6/2007 |
| ZA | 888414 | 10/1988 |

OTHER PUBLICATIONS

U.S. Appl. No. 10/280,937, filed Oct. 25, 2005.
Fechner et al. *Iris-claw lens in phakic eyes to correct hyperopia: preliminary study. J. Cataract Refract. Surg.*, Jan. 24, 1998.
Mandell, *Contact Lens Practice*, 4$^{th}$ Ed.
Menezo et al. *Endothelial study of iris-claw phakic lens: four year follow-up. J. Cataract Refract. Surg.*, Aug. 24, 1998.
Thornton, *Accommodation in Pseudophakia*, 25, p. 159.
AMO Specs, Model AC-21B, 1992.
Study Design of Nuvita, Mar. 20, 1997.
Program from ASCRS Symposium showing video tape between Apr. 10-14, 1999.
DVD titled "New elliptical accommodative IOL for cataract surgery" shown at ASCRS Symposium on Apr. 10, 1999.
English translation of WO 93/05733 Al.
U.S. Appl. No. 09/656,661, filed Sep. 7, 2000.
U.S. Appl. No. 09/721,072, filed Nov. 22, 2000.

\* cited by examiner

SECTION A-A

SECTION B-B

SECTION A-A

SECTION B-B

SECTION B-B

INTRAOCULAR LENS HAVING A HAPTIC THAT INCLUDES A CAP

BACKGROUND OF THE INVENTION

1. Field of the Invention

This invention relates generally to intraocular lenses, and more specifically to accommodating intraocular lenses.

2. Description of the Related Art

A humans eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange.

The simplest IOLs have a single focal length, or, equivalently, a single power. Unlike the eye's natural lens, which can adjust its focal length within a particular range in a process known as accommodation, these single focal length IOLs cannot accommodate. As a result, objects at a particular position away from the eye appear in focus, while objects at an increasing distance away from that position appear increasingly blurred.

An improvement over the single focal length IOLs is an accommodating IOL, which can adjust its power within a particular range. More specifically, an accommodating intraocular lens may change its shape (power) and/or position, so that objects at prescribed distances will be clearly imaged at the plane of the retina. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accommodation range itself is defined as the near power minus the far power. In general, an accommodation range of 4 diopters is considered sufficient for most patients.

The human eye contains a structure known as the capsular bag, which surrounds the natural lens. The capsular bag is transparent, and serves to hold the lens. In the natural eye, accommodation is initiated by a series of zonular fibers, also known as zonules. The zonules are located in a relatively thick band mostly around the equator of the lens, and impart a largely radial force to the capsular bag that can alter the shape and/or the location of the natural lens and thereby change its power.

In a typical surgery in which the natural lens is removed from the eye, the lens material is typically broken up and vacuumed out of the eye, but the capsular bag is left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which reflects light that passes through it and forms an image on the retina, and a haptic, which is a structure that mechanically couples the optic to the capsular bag. During accommodation, the zonules exert a force on the capsular bag, which in turn exerts a force on the optic. The force may be transmitted from the capsular bag directly to the optic, or from the capsular bag through the haptic to the optic.

A desirable optic for an accommodating IOL is one that distorts in response to a squeezing or expanding radial force applied largely to the equator of the optic (i.e., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

One challenge in implementing such an optic is designing a suitable haptic to couple the optic to the capsular bag. The haptic should allow distortion of the optic in an efficient manner, so that a relatively small zonular force can produce a relatively large change in power and/or axial location of the image. This reduces fatigue on the eye, which is highly desirable.

Accordingly, there exists a need for an intraocular lens having a haptic with increased efficiency in converting a zonular force to a change in power and/or a change in axial location of the image.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 20 figures, with like numerals indicating like parts.

DETAILED DESCRIPTION OF THE DRAWINGS

In a healthy human eye, the natural lens is housed in a structure known as the capsular bag. The capsular bag is driven by zonular fibers (also known as zonules) in the eye, which can compress and/or pull on the capsular bag to change its shape. The motions of the capsular bag distort the natural lens in order to change its power and/or the location of the image, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the zonules, it is desirable that the implanted intraocular lens change its power and/or the location of the image in a manner similar to that of the natural lens. Such an accommodating lens may produce vastly improved vision over a lens with a fixed power and location that does not accommodate.

Figure 1:
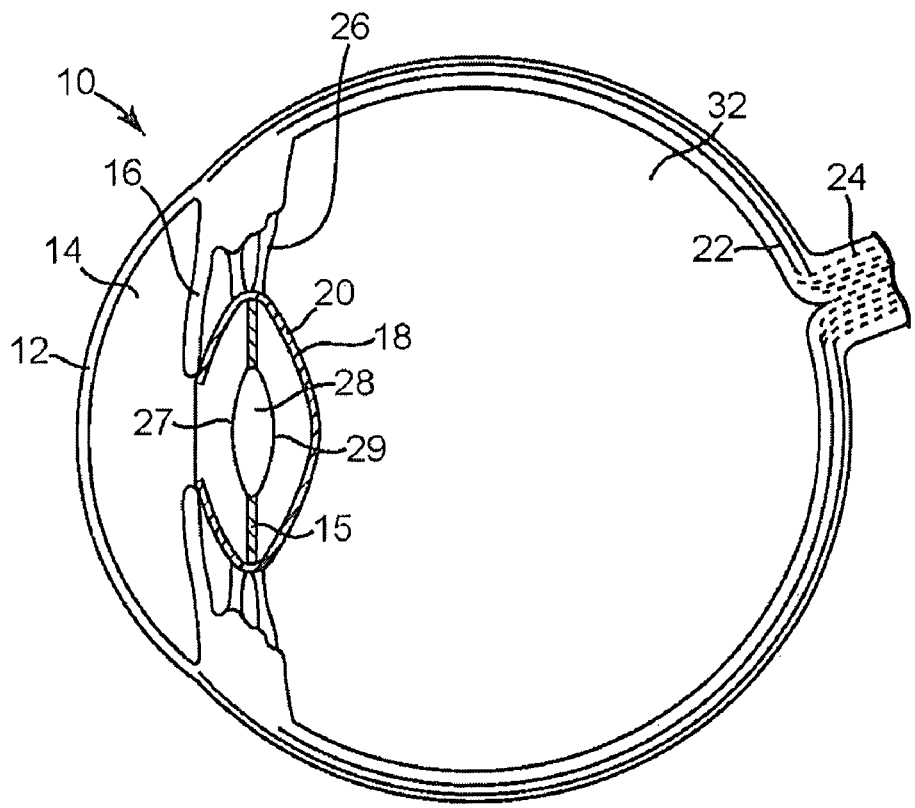
FIG. 1 is a plan drawing of a human eye having an implanted intraocular lens, in an accommodative "near" state.

FIG. 1 shows a human eye 10, after an accommodating intraocular lens according to an embodiment of the present invention has been implanted into the eye of a subject. Light enters from the left of FIG. 1, and passes through the cornea 12, the anterior chamber 14, the iris 16, and enters the capsular bag 18. Prior to surgery, the natural lens occupies essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

A well-corrected eye forms an image at the retina 22. If the lens has too much or too little power, the image shifts axially along the optical axis away from the retina, toward or away from the lens. Note that the power required to focus on a close or near object is more than the power required to focus on a distant or far object. The difference between the "near" and "far" powers is known typically as the range of accommodation. A normal range of accommodation is about 4 diopters, which is considered sufficient for most patients.

The capsular bag is acted upon by the zonules 26, which distort the capsular bag 18 by compressing and/or stretching it radially in a relatively thick band about its equator. Experimentally, it is found that the zonules typically exert a total force of up to about 10 grams of force, which is distributed generally uniformly around the equator of the capsular bag 18. Although the range of zonule force may vary from patient to patient, it should be noted that for each patient, the range of accommodation is limited by the total force that the zonules 26 can exert. Therefore, it is highly desirable that the intraocular lens be configured to vary its power over the full range of accommodation, in response to this limited range of forces exerted by the zonules. In other words, it is desirable to have a relatively large change in power for a relatively small driving force.

Note that the lens may be designed so that its relaxed state is the "far" condition, sometimes referred to as "disaccommodative biased", the "near" condition, "accommodative biased", or some condition in between the two.

The intraocular lens itself has two primary components: an optic 28, which is made of a transparent, deformable and/or elastic material, and a haptic 15, which holds the optic 28 in place and mechanically transfers forces on the capsular bag 18 to the optic 28.

Note that either or both of the haptic 15 and optic 28 may include relatively complex structures that can blur the distinction between the two. For instance, the optic may be made from a soft material, and may include a harder shell-like coating on at least one of the opposite faces of the optic disposed about the optical axis, namely the anterior and/or posterior surfaces. This coating may be made from the same material as the haptic and may or may not be made integral with the haptic. One may argue that such a coating is part of the haptic, since it may be made from the same material as the haptic. Likewise, one may argue that it resides on an optical surface and plays a role in the focusing functions of the lens, and may therefore be considered part of the optic. For the purposes of this document, the strict distinction between haptic and optic is relatively unimportant, and any elements that share a role in the optical and mechanical functions of the lens may be considered to be part of the optic, part of the haptic, or both.

When the eye 10 is focused on a relatively close object, as shown in FIG. 1, the zonules 26 compress the capsular bag 18 in a relatively thick band about its equator. The capsular bag 18 changes shape, becoming thicker at its center and having more steeply curved sides. As a result of this action, the power of the lens increases (i.e., one or both of the radii of curvature can decrease, and/or the lens can become thicker, and/or the lens may also move axially), placing the image of the relatively close object at the retina 22. Note that if the lens could not accommodate, the image of the relatively close object would be located behind the retina, and would appear blurred.

Figure 2:
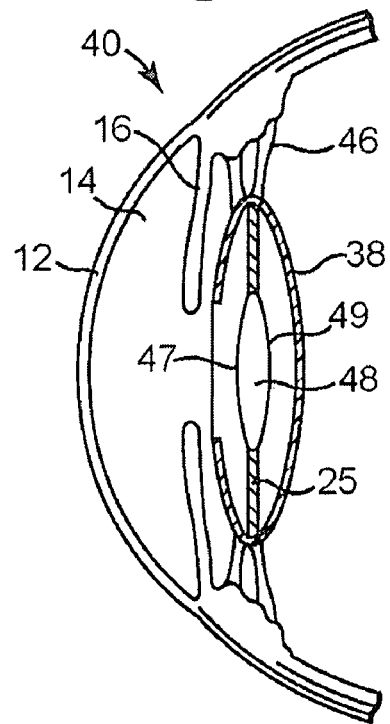
FIG. 2 is a plan drawing of the human eye of FIG. 1, in an accommodative "far" state.
Figure 3:
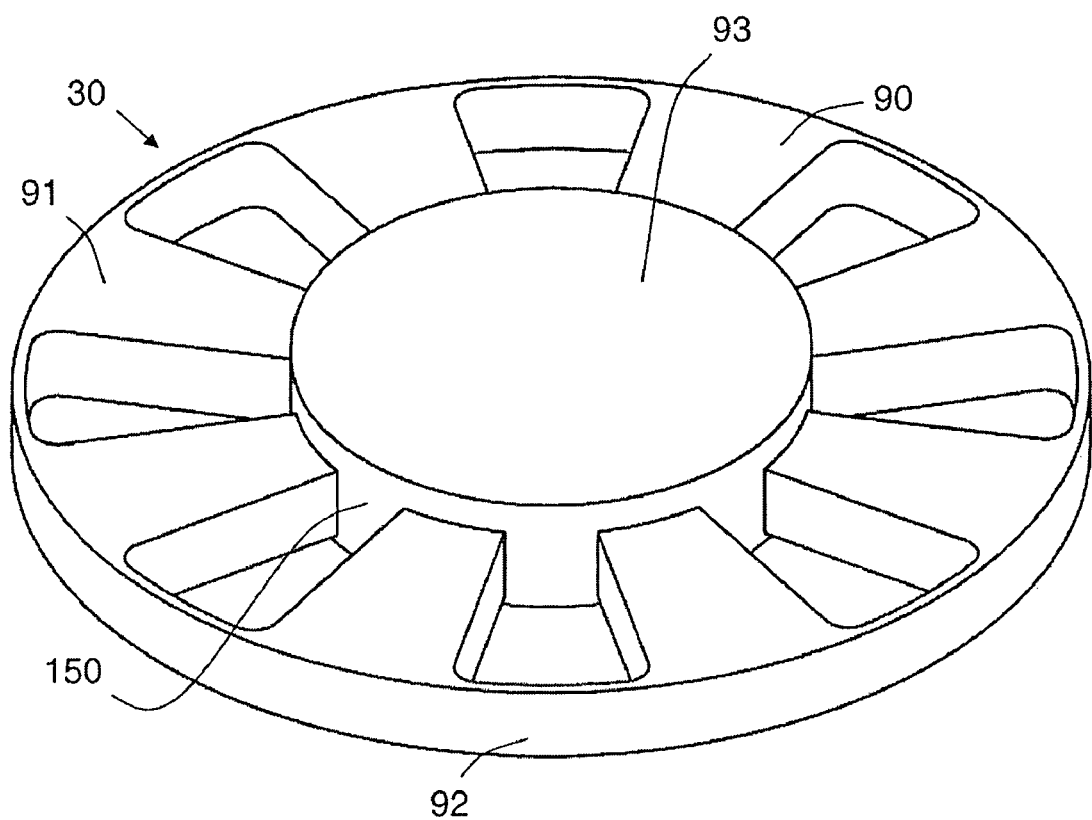
FIG. 3 is an anterior isometric drawing of a haptic/optic assembly.
Figure 4:
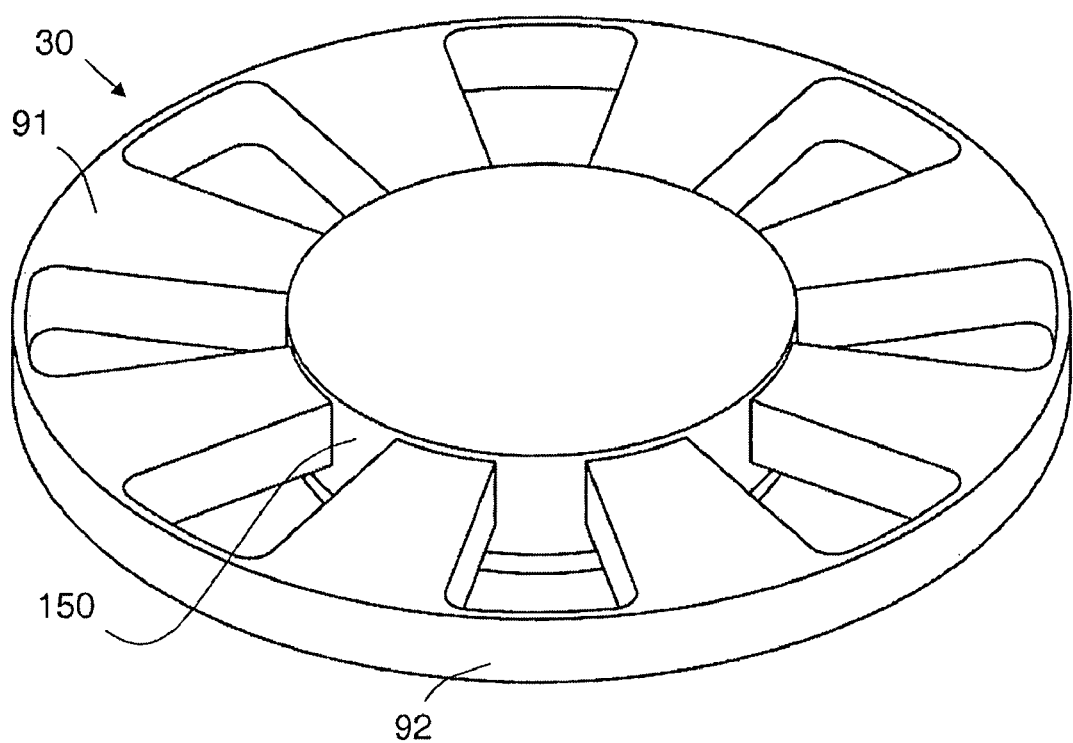
FIG. 4 is a posterior isometric drawing of a haptic/optic assembly.

FIG. 2 shows a portion of an eye 40 that is focused on a relatively distant object. The cornea 12 and anterior chamber 14 are typically unaffected by accommodation, and are generally similar to the corresponding elements in FIG. 1. To focus oil the distant object, the zonules 46 retract and change the shape of the capsular bag 38, which becomes thinner at its center and has less steeply curved sides. This reduces the lens power by flattening (i.e., lengthening radii of curvature and/or thinning) the lens, placing the image of the relatively distant object at the retina (not shown).

In the illustrated embodiment of FIGS. 1 and 2, near and distant vision are both generally provided as the intraocular lens responds to shape changes in the capsular bag. In certain embodiments, the intraocular lens may be configured to have a disaccommodative bias, wherein the power of the optic 28 is generally selected to provide distant vision when haptic 50 and optic 28 are in a natural or unstressed state (i.e., when there are substantially no external forces on the intraocular lens). In such embodiments, the intraocular lens is in a natural state when the ciliated muscle is relaxed, thereby pulling on the zonules and capsular bag. In this state, the radius of curvature of the anterior face 47 and/or posterior face 49 are generally relatively large, which results in a relatively low lens power. For near vision, the ciliary muscle contracts and the haptic 50 and optic 28 are compress by the capsular bag as tension on the zonules is reduced. In this stressed state of the optic 28, the radius of curvature is decreased, thus increasing the lens power.

In other embodiments, the intraocular lens may be configured to have an accommodative bias, wherein the power of the optic 28 is selected to provide near vision when haptic 50 and optic 28 are in a natural or unstressed state. In such embodiments, the intraocular lens is in a natural state when the ciliary muscle contracts to relax the zonules and capsular bag. In this state, the radius of curvature of the anterior face 47 and/or its posterior face 49 is relatively small, which results in a relatively high lens power. For distant vision, the ciliary muscle relax, which pulls on the zonules, capsular bag, the haptic 50, and optic 28. In this stressed state of the optic 28, the radius of curvature is increased, thus decreasing the lens power. Alternatively, the optic 28 may be selected to have an intermediate power between near and distant when in a natural or unstressed state. In such embodiments, the haptic 50 and optic 28 may be both compressed and stretched to provide near and distant vision, respectively.

Note that the specific degrees of change in curvature of the anterior and posterior faces depend on the nominal curvatures. Although the optics 28 and 48 are drawn as bi-convex, they may also be plano-convex, meniscus or other lens shapes, where the anterior and posterior faces may each be convex, concave or planar. In all of these cases, the optic is compressed or expanded by essentially radial forces by the haptic to the edge and/or faces of the optic. In addition, the may be some axial movement of the optic. In some embodiments, the haptic is configured to transfer the generally symmetric radial forces symmetrically to the optic to deform the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optics may optionally have one or more diffractive elements, one or more multifocal elements, and/or one or more aspheric elements.

An exemplary intraocular lens is shown in detail in FIGS. 3-20, which show a similar series of views for the haptic/optic assembly 30 (FIGS. 3-8), only the haptic 90 (FIGS. 9-14), and only the optic 150 (FIGS. 15-20). Each Of the six figures for the haptic/optic assembly 30, the haptic 90 and optic 150 shows, in order, an anterior isometric drawing, a posterior isometric drawing, a front view drawing, a section view A-A drawing, a top view drawing and a section view B-B drawing.

The intraocular lens may be generally saucer- or capsule-shaped, lying essentially in a plane perpendicular to the optical axis of the lens. The haptic 90 may have an optional, generally circular outer edge 92 extending around the equator of the lens, which couples the lens to the capsular bag of the eye. Alternatively, there may be additional features and/or discontinuities along the outer edge 92.

Figure 7:
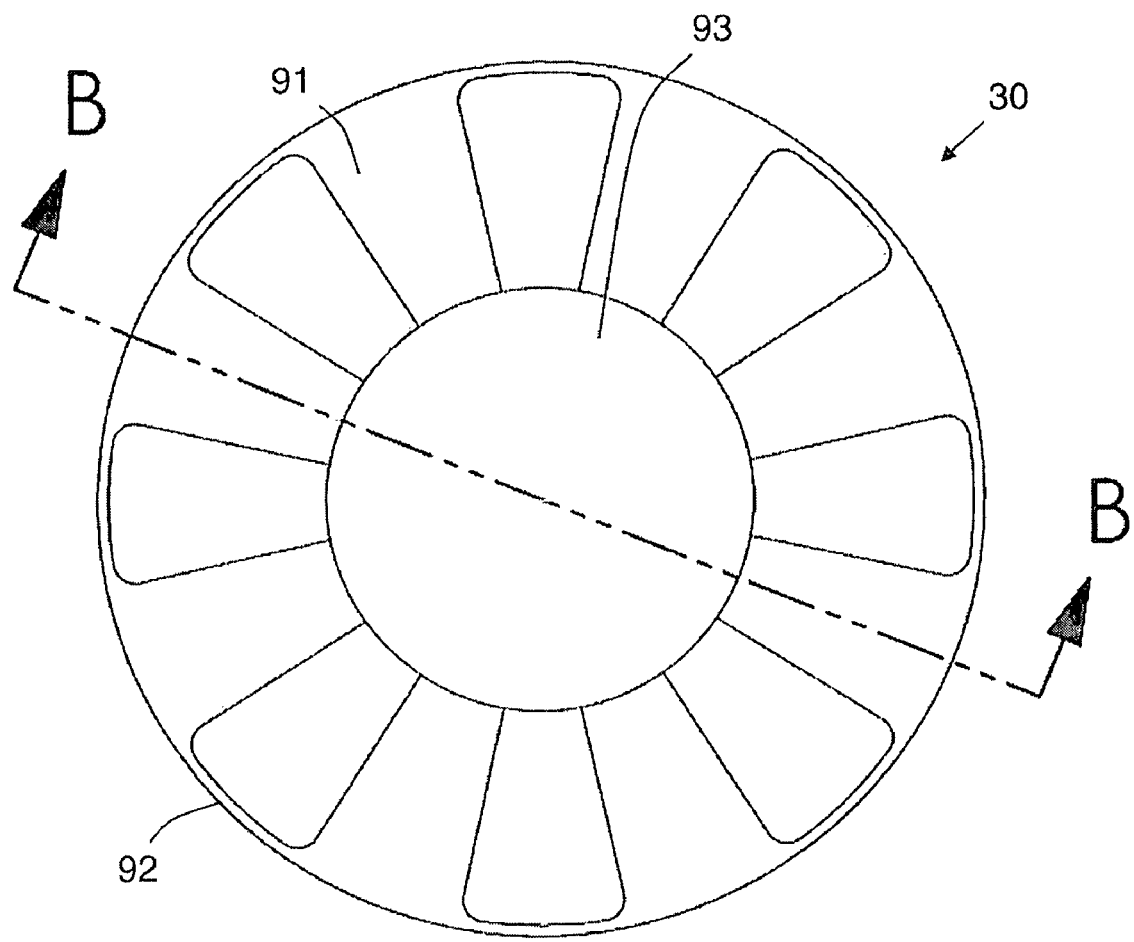
FIG. 7 is a top view drawing of a haptic/optic assembly.
Figure 8:
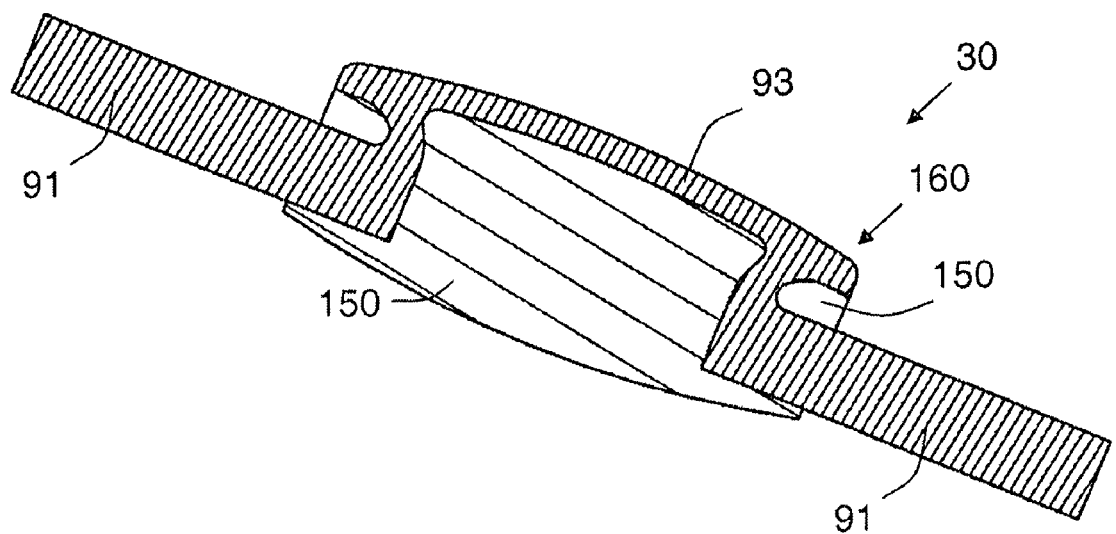
FIG. 8 is a section view B-B drawing of a haptic/optic assembly.
Figure 9:
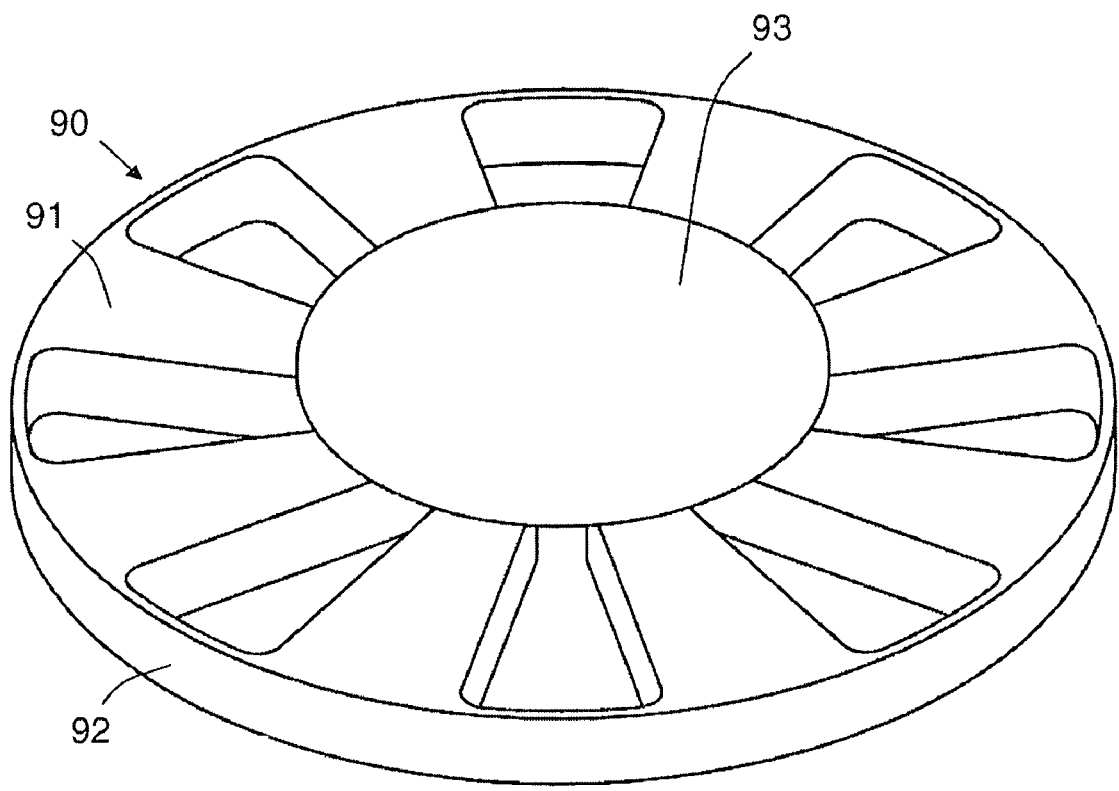
FIG. 9 is an anterior isometric drawing of the haptic of FIGS. 3-8.
Figure 10:
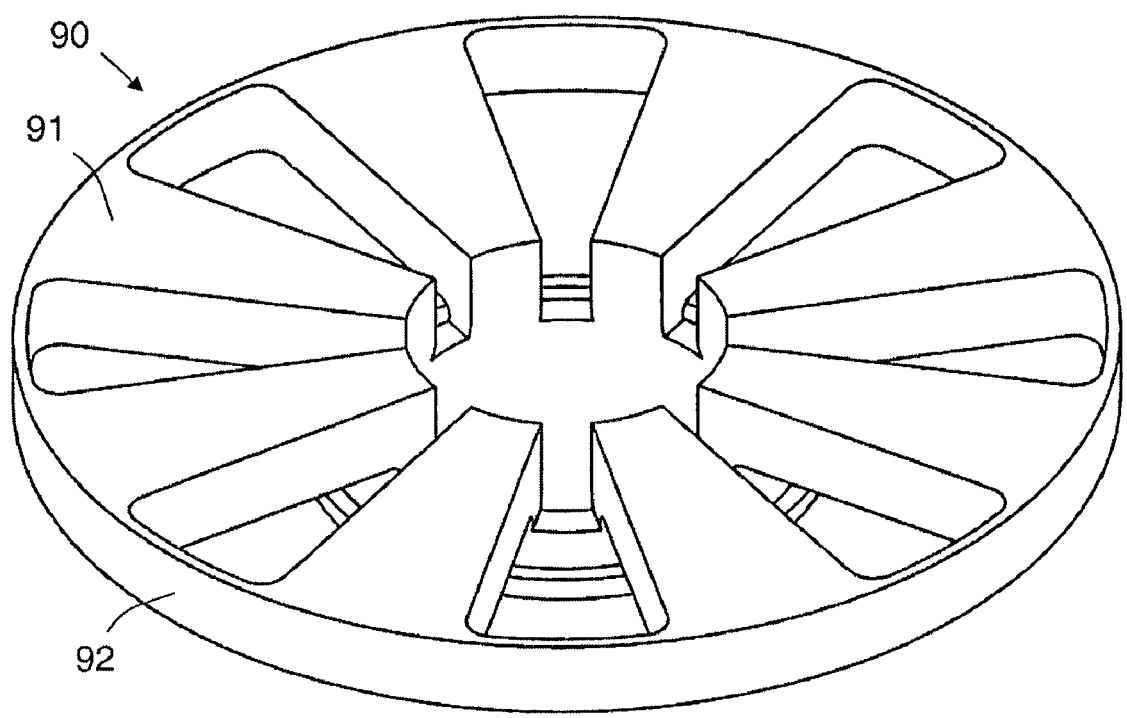
FIG. 10 is a posterior isometric drawing of the haptic of FIGS. 3-8.
Figure 11:
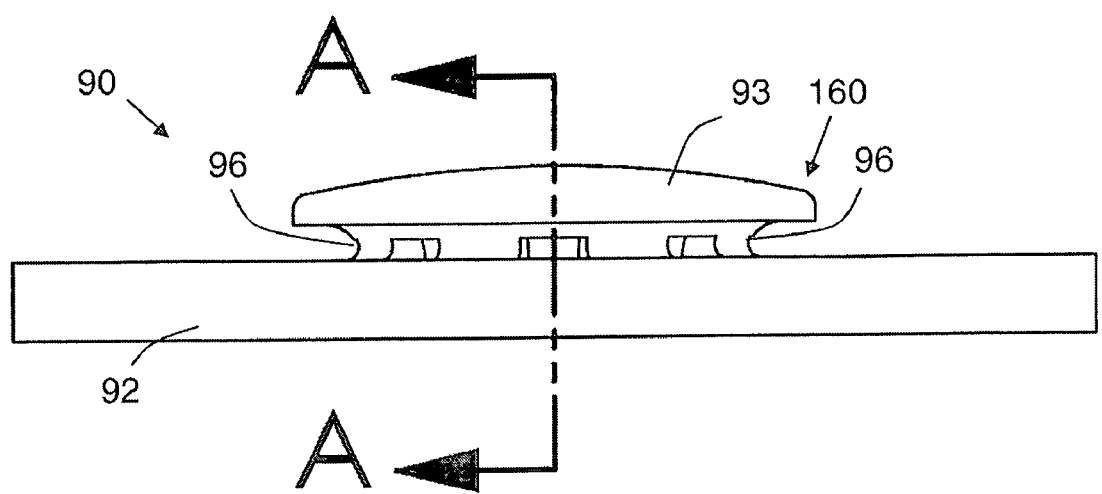
FIG. 11 is a front view drawing of the haptic of FIGS. 3-8.
Figure 12:
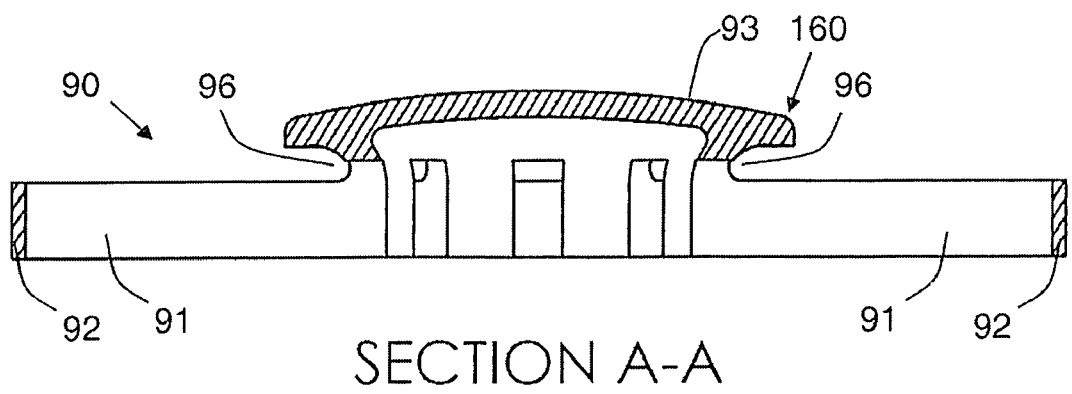
FIG. 12 is a section view A-A drawing of the haptic of FIGS. 3-8.
Figure 13:
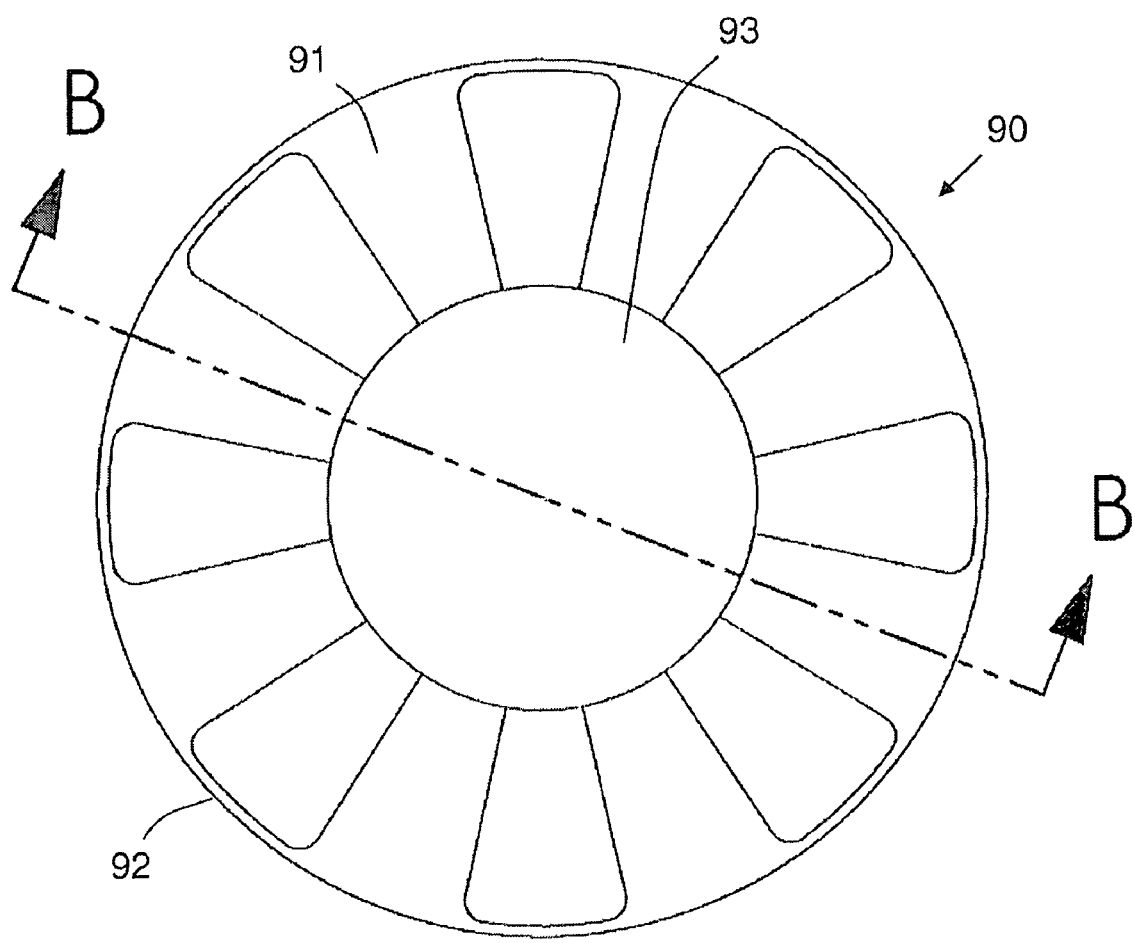
FIG. 13 is a top view drawing of the haptic of FIGS. 3-8.
Figure 14:
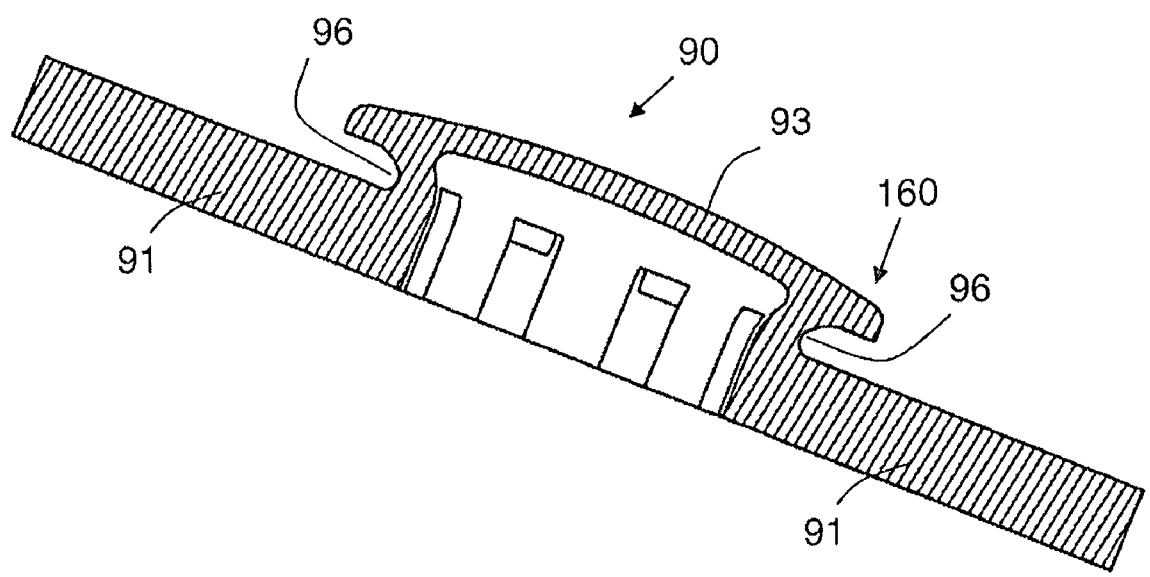
FIG. 14 is a section view B-B drawing of the haptic of FIGS. 3-8.
Figure 15:
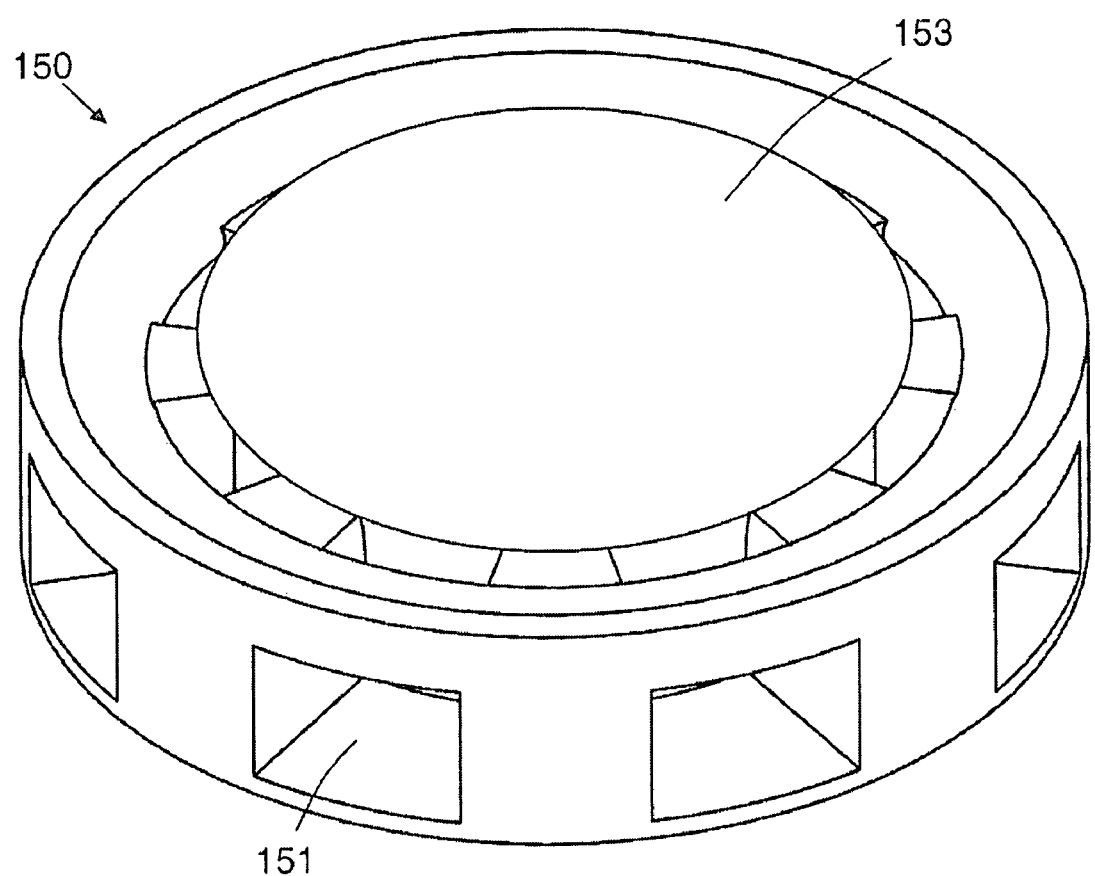
FIG. 15 is an anterior isometric drawing of the optic of FIGS. 3-8.
Figure 16:
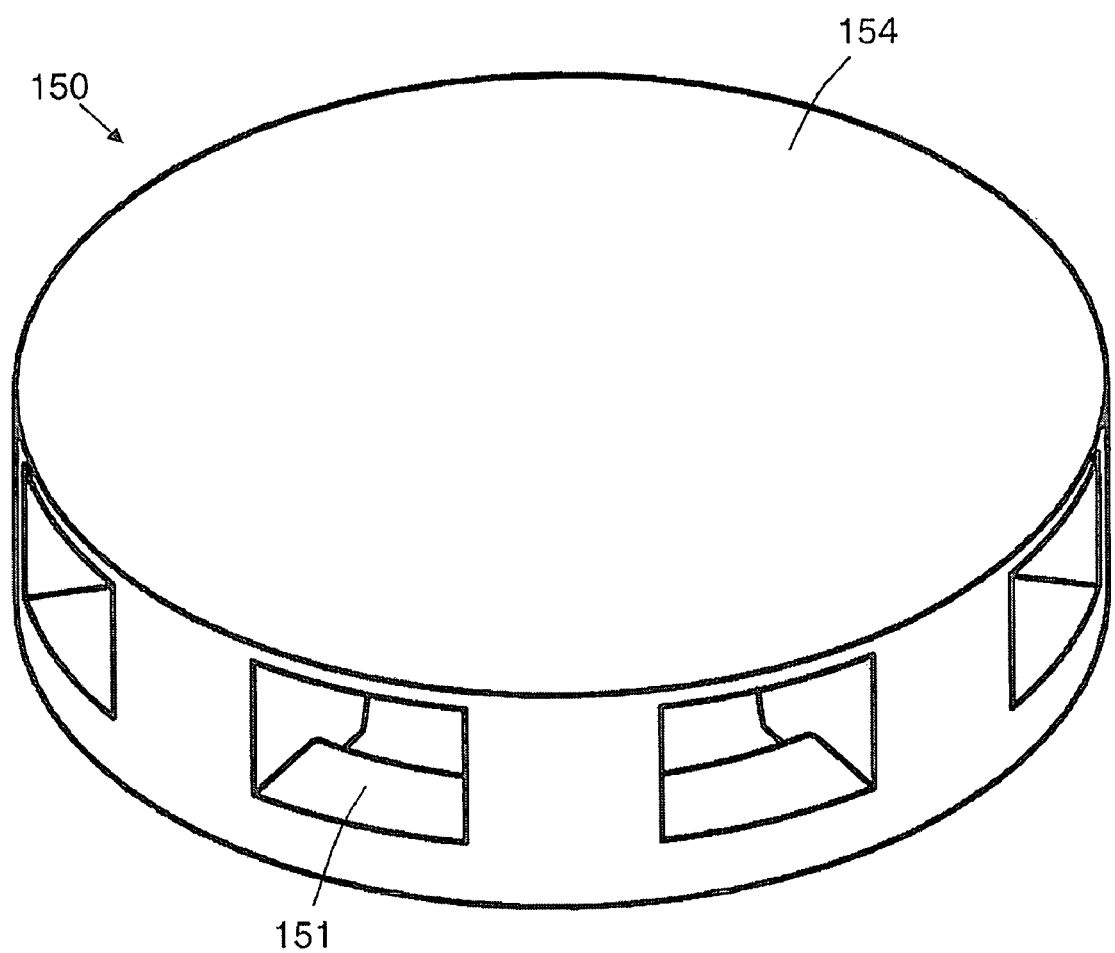
FIG. 16 is a posterior isometric drawing of the optic of FIGS. 3-8.
Figure 17:
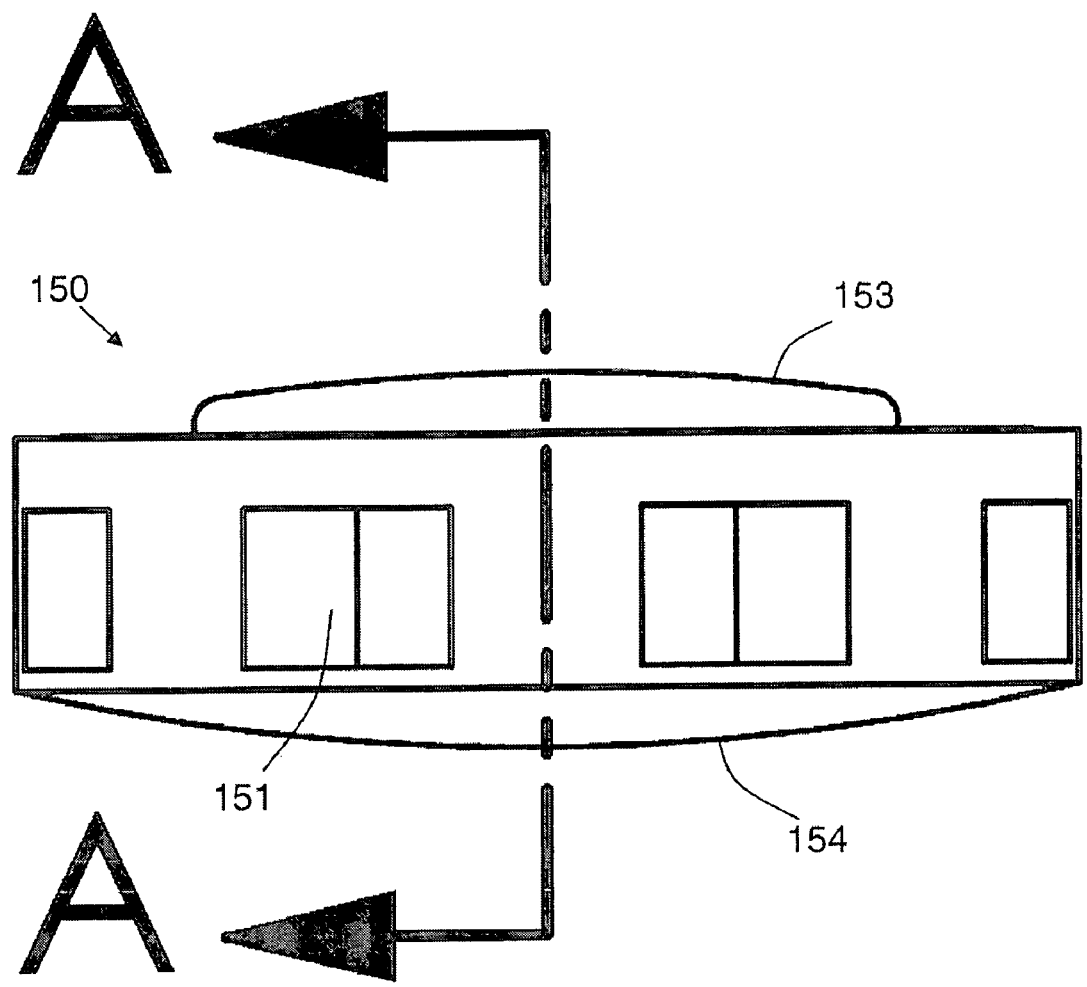
FIG. 17 is a front view drawing of the optic of FIGS. 3-8.
Figure 18:
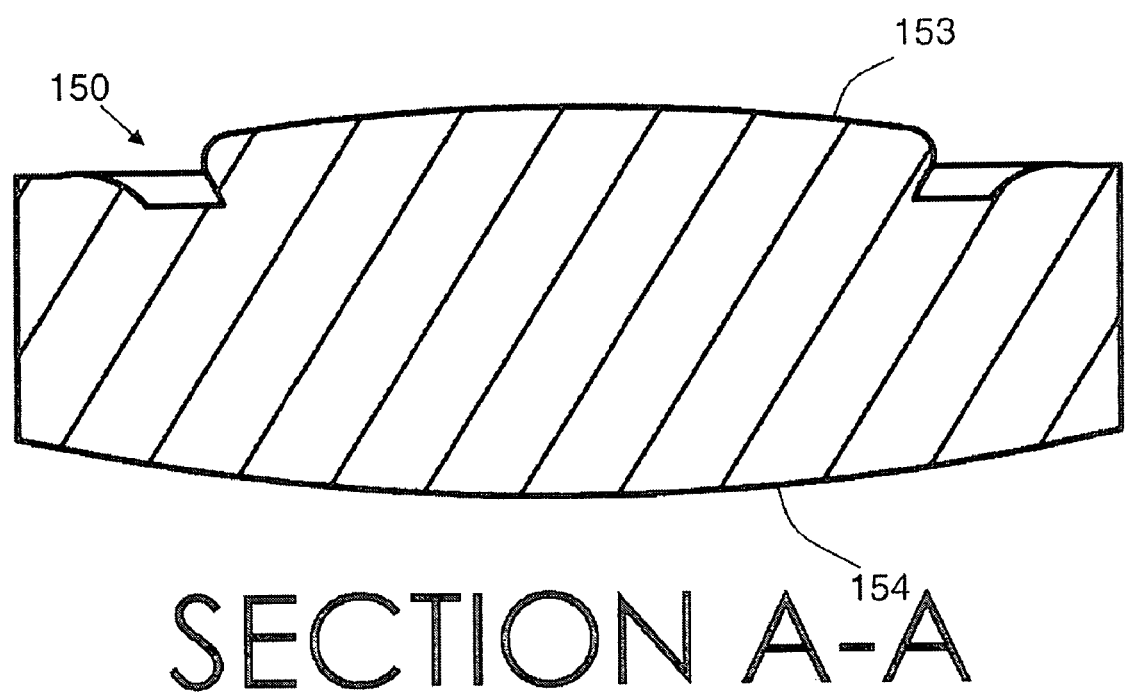
FIG. 18 is a section view A-A drawing of the optic of FIGS. 3-8.
Figure 19:
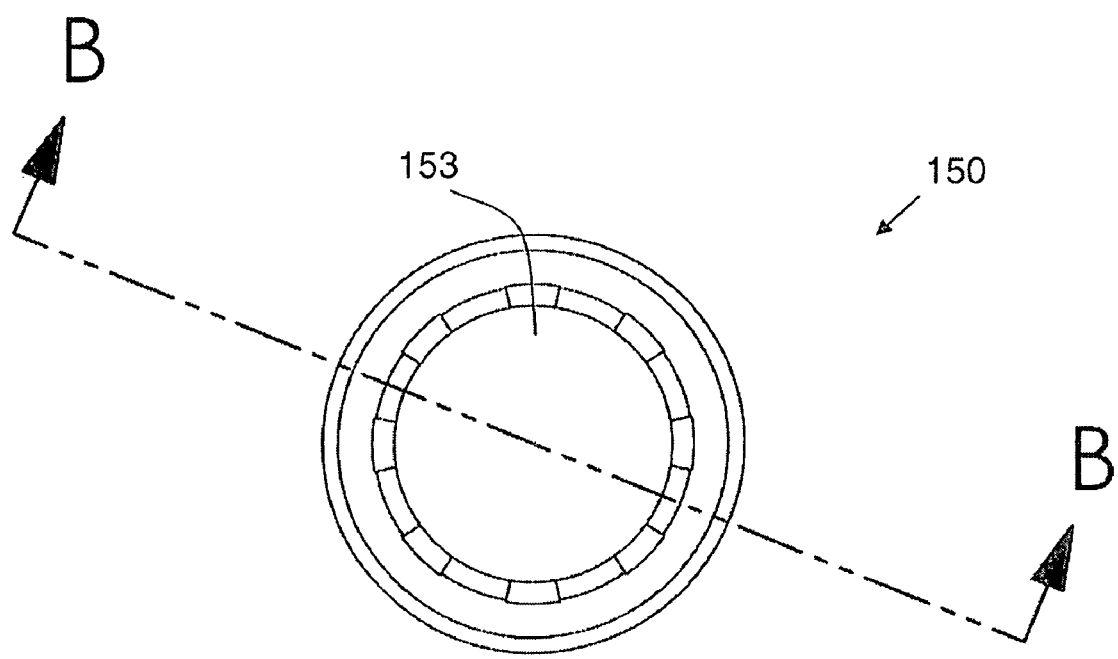
FIG. 19 is a top view drawing of the optic of FIGS. 3-8.
Figure 20:
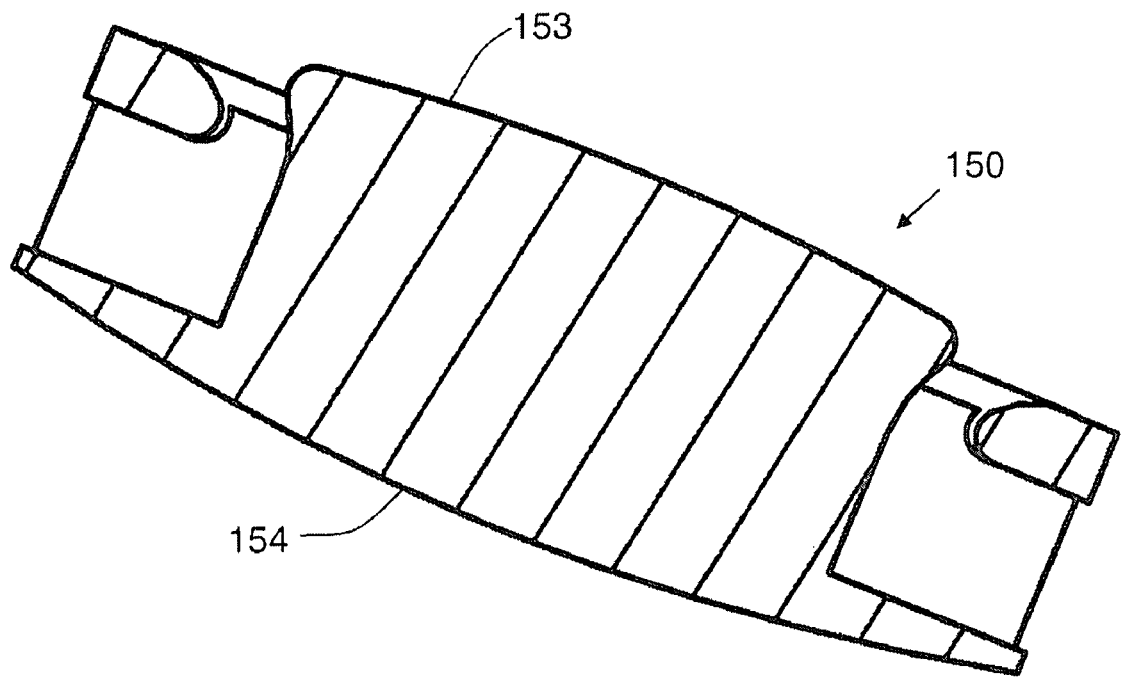
FIG. 20 is a section view B-B drawing of the optic of FIGS. 3-8.

From a top view, such as in FIG. 7, the haptic/optic assembly 30 appears similar to a wagon wheel, with individual haptic "spokes" or arms 91 radiating from a central optic cap towards a thin, continuous outer ring. From a cut-away side view, such as in FIG. 8, one sees that the central optic cap may be a thin, continuous membrane that balloons up from the haptic arms and forms a mushroom-like shape. The haptic 90 and optic 150 are described in greater detail below.

The haptic 90 may have various arms 91 or filaments extending radially from the outer edge 92 to the optic 150, located at or near the center of the lens. The haptic arms 91 may each be wedge-shaped, within the plane of the haptic 90, increasing in in-plane width from the inner portion to the outer edge of the haptic. Alternatively, the haptic arms 91 may have a constant in-plane width or an increasing in-plane width in all or portions, from the outer edge to the inner portion. The spaces between the haptic arms 91 may also be wedge-shaped, and may alternately include portions of constant in-plane width or increasing in-plane width, from the outer edge 92 to the inner portion.

The haptic arms 91 may be all connected at the outer edge 92 of the haptic 90. In some embodiments, the outer edge 92 may connect the arms 91 with a thin tangential portion having a radial thickness smaller than the tangential thickness of the haptic alms 91 themselves.

Figure 5:
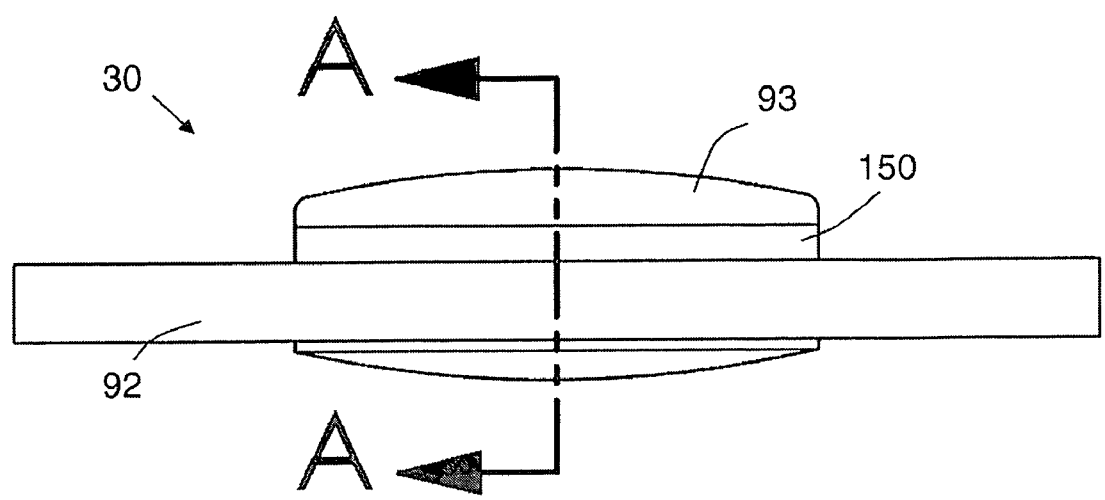
FIG. 5 is a front view drawing of a haptic/optic assembly.
Figure 6:
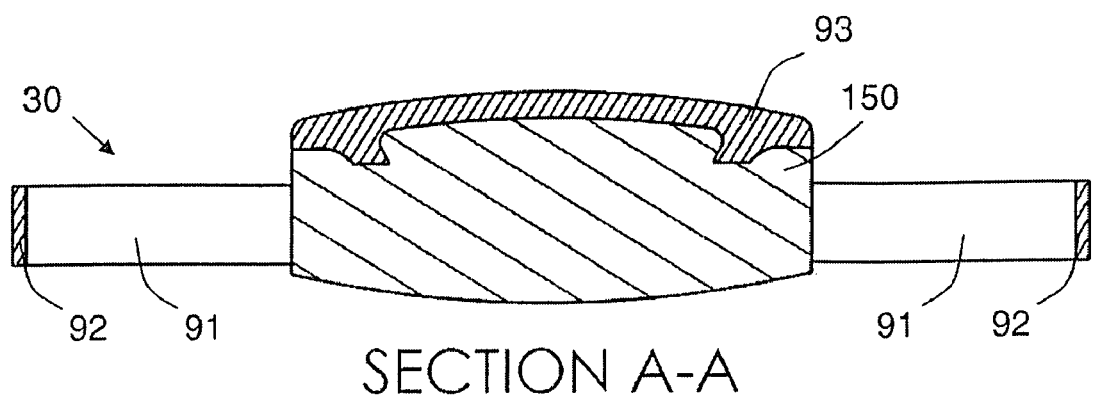
FIG. 6 is a section view A-A drawing of a haptic/optic assembly.

The haptic 90 itself may be essentially planar when seen from the side, as in FIG. 5, and may include generally flat and parallel anterior and posterior surfaces. Alternatively, the anterior and posterior surfaces of the haptic 90 may be tilted, inclined or curved.

The intraocular lens further includes a cap 93 that extends over the anterior surface 153 of the optic 150. Alternatively, the cap 93 may extend over the posterior surface 154 of the lens. At the inner portion of the lens, the haptic arms 91 may connect to each other and/or to the cap 93. See, for instance, FIG. 8, which shows a cross-sectional view of the haptic 90 and the optic 150, and FIG. 14, which shows the same view but without the optic 150.

Note that the cap 93 may have a uniform thickness over its surface, or may optionally have a valuable thickness over its surface. For instance, the cap 93 may be thicker in its center, near the optical axis of the lens, than at its periphery. Alternatively, the cap 93 may be thinner at its center than at its periphery. In general, the shape of the cap 93 over its surface helps determine the anterior and posterior surface shapes of the cap and the optic at each particular power within the accommodation range. In other words, the thickness may optionally vary over the surface of the cap, so that the capped surface shape deforms in a prescribed manner during accommodation. For instance, the cap 93 may include one or more aspheric and/or conic terms in its surface profile and/or its transmitted wavefront profile, which may help reduce aberrations in the optical system of the eye at one or more points within the range of accommodation.

In some embodiments, the cap is stiffer than the optic, so that if an anterior cap were not present, the curvature of the optic anterior surface would vale more during accommodation, compared to having the anterior cap present. This change in surface curvature may be affected by the stiffness of the cap, so that a more stiff cap deforms less during accommodation than a less stiff cap, for comparable cap shapes. The surface deformation may also be affected by varying the thickness of the cap, so that a relatively thick cap may deform less than a relatively thin cap, for comparable material moduli.

In some embodiments, the presence of a cap on the anterior face of the lens may help ensure that the lens vaults in the anterior direction during accommodation. More specifically, if a lens having an anterior cap is squeezed radially around its equator by the capsular bag, the cap may help ensure that at least one of the lens surfaces translates away from the retina.

Note that near the innermost portion of the lens, each haptic arm 91 includes an out-of-plane, curved portion 96, in which the haptic arm 91 protrudes out of the plane of the haptic 90 and attaches to the cap 93. This haptic detail is seen most clearly in the haptic-only pictures in FIGS. 9-14.

The out-of-plane curved portion 96 may be considered to be part of a so-called "coupling member-" or "force transfer member" 160, which mechanically couples the generally planar structure of the haptic 90 to the cap 93. As the capsular bag changes shape and/or size, the haptic airs 91 compress or expand radially, and the force transfer member 160 couples this radial compression or expansion to the cap 93. It may be helpful to think of the force transfer member 160 as being analogous to a hinge, with a bending occurring at the out-of-plane curved portion 96. The force transfer member 160 may optionally include a portion around the circumference of the cap, which extends radially beyond the out-of-plane curved portion 96. In general, the shape and features of the force transfer member 160 helps determine the anterior and posterior surface shapes of the cap and the optic at each particular power within the accommodation range.

Note that when the optic 150 is present, the optic 150 obscures much of the inner detail of the haptic 90, as seen from FIGS. 3-5 and 7. This is most easily understood from an explanation of an exemplary manufacturing process for the lens. First, the haptic is produced by a molding process. Next, the optic is inserted onto/into the haptic by a second molding process, in which the softer optic material fills the cap 93 and encapsulates a portion of the haptic arms. The optic extends posteriorly out of the general plane of the haptic arms, and forms an essentially continuous posterior surface 154 to the optic 150. When viewed from the edge, as in FIG. 5, the assembled haptic/optic assembly therefore has a cap 93 made from the haptic material, and an optic 150 that extends from the cap 93 through the plane of the haptic 90 to the posterior surface 154 of the optic 150. The anterior surface 153 of the optic 150 is hidden in this assembled view, and is generally flush with the cap 93 of the haptic 90. The optic 150, when viewed separately from the haptic 90, may include various holes 151 that accommodate the haptic arms 91, and several other features on or near its anterior side; ultimately it is easiest to describe the shape of the optic as filling in a central portion of the lens and occupying a particular volume that is not occupied by the haptic itself.

The optic 150 and the haptic 90 may generally be constructed of any of the various types of material known in the art. For example, the optic 150 and/or the haptic 90 may be of a resiliently deformable or foldable material such as silicone polymeric materials, acrylic polymeric materials, hydrogel-forming polymeric materials (e.g., polyhydroxyethyl-methacrylate, polyphosphazenes, polyurethanes, and mixtures thereof), and the like. Other advanced formulations of silicone, acrylic, or mixtures thereof are also anticipated. Selection parameters for suitable lens materials are well known to those of skill in the art. See, for example, David J. Apple, et al., Intraocular Lenses: Evolution, Design. Complications, and Pathology, (1989) William & Wilkins, which is herein incorporated by reference. The optic and/or haptic materials may be selected to have a relatively high refractive index, and thus provide a relatively thin optic, for example, having a center thickness in the range of about 150 microns to about 1000 microns, depending on the material and the optical power of the lens.

The haptic 90 and/or the cap 93 may be generally stiffer than the optic. In some embodiments, the haptic 90 and/or the cap 93 are made stiffer by selecting a material with a higher modulus than that of the optic 150 material. For instance, the haptic/cap material may have a typical modulus of elasticity in the range of 500-1500 kPa or greater, while a typical optic material may have a modulus that is less than 500 kPa, less than 100 kPa, or within the range of 25 kPa to 50 kPa. The haptic material and optic material may both be transparent, so that light may transmit through the cap 93 of the haptic 90, and so that the haptic arms 91 may occupy a portion of the pupil of the lens without obstructing any light.

It may be preferable to have the refractive index of the haptic 90 material be matched to that of the optic 150 material, which may reduce or minimize any reflections that arise at the interfaces between the haptic 90 and optic 150. Alternatively, the refractive indices of the haptic material may be selected to be different from that of the optic material. Additionally or alternatively, the dispersion of the haptic and optic materials may be selected to be different, for example, to provide at least some chromatic collection to light entering the eye of a subject into which the optic 150 is placed. A typical range for these refractive indices is about 1.43 to about 1.56, although any suitable range may be used. In general, the haptic and the optic may be considered to be "refractive index-matched" if their refractive indices are equal for at least one wavelength that lies within the visible spectrum, or between 400 nm and 700 nm. A typical center thickness for the optic is in the range of about 2.0-2.5 mm. A typical edge thickness for the optic is in the range of about 1.0-1.5 mm.

There are several advantages to the exemplary haptic/optic assembly 30 shown in FIGS. 3-20, compared to known accommodating intraocular lenses that lack a cap 93.

A first advantage is that during accommodation, the axial movement of the lens may be biased anteriorly. In its relaxed state, in which the eye is focused on a distant object, the zonular fibers and the capsular bag of the eye are expanded radially around the equator of the intraocular lens, and the haptic remains largely in a single plane, as in FIG. 5. In its accommodative state, in which the eye is focused on a relatively close object, the zonular fibers and the capsular bag of the eye are compressed radially around the equator of the intraocular lens. The haptic develops a cone-like shape, in which its equator remains coincident with the capsular bag and its central portion is bowed out in the anterior direction. In this bowed-out state, the optic may translated away from its "relaxed" position, with the translation occurring in the anterior direction. In other words, when the eye focuses on a close object, the optic may be translated away from the retina. This anterior translation during accommodation assists the optic in focusing a "near" image on the retina, and eases the forces required from the zonular fibers for a particular accommodation range. In contrast, a posterior translation would work against the optic, and would require a significantly larger force exerted by the zonular fibers on the capsular bag for a similar accommodation range.

A second advantage is that the anterior cap may protect the relatively soft optic material. The anterior cap may be made from the haptic material, which may be significantly stiffer or harder than the optic material. As a result, the relatively soft anterior surface of the optic may be protected by the anterior cap, and may be less susceptible to damage such as scratching during installation. In addition, because the optic material may be relatively tacky or sticky, the layer of haptic material in the anterior cap may improve the ability to handle the lens by reducing the area of exposed tacky optic material.

A third advantage is that the power change of the lens arises primarily from the deformation of the anterior surface of the optic, while the posterior surface does not include a porter change that significantly offsets that from the anterior surface. In other words, the posterior surface may deform slightly during accommodation, but the power change of the posterior surface may be relatively small and/or may aid in accommodation. In contrast, if the power change of the posterior were to partially offset the increase in power of the full lens for accommodation, then a larger force would be required of the zonular fibers and capsular bag in the eye, for a particular range of accommodation.

In one embodiment, the lens may include a posterior cap of haptic material over the posterior surface of the lens. This optional posterior cap may protect the posterior surface of the optic, and may ease the handling requirements of the optic before and during installation. This posterior cap may be thinner than the anterior cap, or may alternatively be the same thickness or thicker than the anterior cap. The thickness may optionally vary over the surface of the posterior cap. The posterior cap may be made of the same material as the anterior cap, or may be may from a different material. The stiffnesses of the anterior and posterior cap may be the same, or may be different.

In one embodiment, the lens may include a posterior cap but no anterior cap.

In one embodiment, the anterior cap may be made from multiple layers, in which one layer may be made from the haptic material, and the other layer or layers may be made from a different material having the same stiffness or a different stiffness.

In one embodiment, the thickness of the anterior cap may vary across the anterior surface. For instance, the center of the cap may be thicker than the edges of the cap. Alternatively, the anterior cap may be essentially uniform over the anterior surface of the optic.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens for implantation in a capsular bag of an eye, comprising:
    an adjustable optic having an anterior face and a posterior face;
    a haptic configured to couple the adjustable optic to the capsular bag;
    a cap adjacent at least one of the anterior and posterior faces of the adjustable optic; and
    the cap being connected to the haptic by a force transfer member separate from the adjustable optic the optic is deformed by radial forces on the haptic through the force transfer member.

2. The intraocular lens of claim 1, wherein the haptic has a stiffness that is greater than a stiffness of the optic.

3. The intraocular lens of claim 2, wherein the haptic has a modulus that is greater than 500 kPa and the adjustable optic has modulus that is less than 500 kPa.

4. The intraocular lens of claim 3, wherein the adjustable optic has a modulus that is less than 100 kPa.

5. The intraocular lens of claim 3, wherein the adjustable optic has a modulus that is between 25 kPa and 50 kPa.

6. The intraocular lens of claim 1, wherein the haptic and adjustable optic are both made from a silicone material or an acrylic material.

7. The intraocular lens of claim 1, wherein the haptic and adjustable optic have refractive indices matched to each other in the range of 1.43 to 1.56.

8. The intraocular lens of claim 1, wherein the cap is integral with the haptic.

9. The intraocular lens of claim 1, wherein the anterior face of the adjustable optic and the posterior face of the adjustable optic are both convex.

10. The intraocular lens of claim 1, wherein one of the anterior face of the adjustable optic and the posterior face of the adjustable optic is planar, and the other of the anterior face of the adjustable optic and the posterior face of the adjustable optic is convex.

11. The intraocular lens of claim 1, wherein one of the anterior face of the adjustable optic and the posterior face of the adjustable optic is convex, and the other of the anterior face of the adjustable optic and the posterior face of the adjustable optic is concave.

12. The intraocular lens of claim 1, further comprising a secondary cap; wherein the cap is adjacent to one of the anterior face of the adjustable optic and the posterior face of the adjustable optic, and the secondary cap is adjacent to the other of the anterior face of the adjustable optic and the posterior face of the adjustable optic.

13. The intraocular lens of claim 12, wherein the cap and the secondary cap are made from materials having different stiffnesses.

14. The intraocular lens of claim 1, wherein the radial force is an ocular force.

15. The intraocular lens of claim 1, wherein the force transfer member includes a hinge.

16. An intraocular lens, comprising:
    an adjustable optic having a first surface and a second surface opposite the first surface; and
    a haptic for supporting the adjustable optic, the haptic comprising:
        a plurality of wedge-shaped haptic arms extending radially outward from the adjustable optic, the haptic comprising gaps between the wedge-shaped haptic arms; and
        a cap extending over and substantially covering the first surface of the adjustable optic and connecting to the haptic arms within the adjustable optic.

17. The intraocular lens of claim 16, wherein the first surface is the anterior surface of the adjustable optic.

18. The intraocular lens of claim 16, wherein the haptic is refractive index-matched to the adjustable optic.

19. The intraocular lens of claim 16, wherein the haptic is stiffer than the adjustable optic.

20. The intraocular lens of claim 16, wherein at least one of the first surface and the second surface of the adjustable optic is convex.

21. The intraocular lens of claim 16, the haptic further comprising a secondary cap extending over the second surface of the adjustable optic, the secondary cap being thinner than the cap over the first surface.

22. The intraocular lens of claim 16, wherein the cap and the haptic are integrally made.

23. The intraocular lens of claim 16, wherein the cap and the haptic are made of the same material.

24. An intraocular lens for implantation in a capsular bag of an eye, comprising:
    an adjustable optic having an outer perimeter, an anterior face and a posterior face; and
    a haptic coupled with the outer perimeter of the adjustable optic for coupling the adjustable optic to the capsular bag, the haptic including a cap having an interior surface for contacting at least one of the faces of the adjustable optic, said haptic comprising a plurality of wedge shaped arms;
    wherein the cap and the haptic are made from the same material;
    wherein the haptic is stiffer than the adjustable optic; and
    wherein the cap is refractive index-matched to the adjustable optic.

25. The intraocular lens of claim 1, wherein the haptic comprises a plurality of arms coupled with the adjustable optic and an outer portion configured to be placed into contact with an inner surface of the capsular bag and to extend between at least two of the arms.

26. The intraocular lens of claim 25, wherein at least some of the plurality of haptic arms comprises a first width adjacent to the outer portion of the haptic and a second width adjacent to the adjustable optic, the first width being greater than the second width.

27. The intraocular lens of claim 1, wherein at least a portion of the force transfer member is positioned inside the optic.

28. The intraocular lens of claim 1, wherein the cap extends continuously across the at least one of the anterior and posterior faces of the adjustable optic.

29. The intraocular lens of claim 1, wherein the cap extends across at least a center portion of the at least one of the anterior and posterior faces of the adjustable optic.

30. The intraocular lens of claim 1, wherein the haptic is disposed along a plane, and wherein the force transfer member includes a portion that protrudes from a radially inner portion of the haptic out of the plane defined by the haptic toward the cap.

31. The intraocular lens of claim 30, wherein the force transfer member includes a portion disposed around the cap that extends radially outwardly of the protruding portion.

32. The intraocular lens of claim 16, wherein the cap extends radially inwardly past a radially outer edge of the adjustable optic.

33. The intraocular lens of claim 16, wherein the cap extends continuously across the first surface of the adjustable optic.

34. The intraocular lens of claim 16, wherein the cap extends across at least a center portion of the first surface of the adjustable optic.

35. The intraocular lens of claim 16, wherein the plurality of wedge-shaped haptic arms are disposed along a plane, and wherein the haptic comprises a connection portion that protrudes out of the plane from a radially inner portion of the haptic arms toward the cap.

36. The intraocular lens of claim 24, wherein cap is coupled to the plurality of wedge shaped arms within the optic.

37. The intraocular lens of claim 24, wherein the cap extends continuously across the at least one of the faces of the adjustable optic.

38. The intraocular lens of claim 24, wherein the cap extends at least across a center portion of the at least one of the faces of the adjustable optic.

39. The intraocular lens of claim 24, wherein the plurality of wedge shaped arms are disposed on a plane, and wherein the haptic comprises a connection portion that protrudes from radially inner portions of the wedge shaped arms out of the plane and toward the cap.

40. The intraocular lens of claim 24, wherein the cap contacts at least one of the faces of the adjustable optic throughout a range of adjustment.

41. The intraocular lens of claim 24, wherein the intraocular lens comprises an accommodated state and an unaccommodated state, the cap contacting at least one of the faces of the adjustable optic in both of the accommodated and unaccommodated states.

* * * * *